United States Patent [19]

Cramer

[11] Patent Number: 4,858,625

[45] Date of Patent: Aug. 22, 1989

[54] SECURITY RESTRAINING BLANKET

[76] Inventor: Judith C. Cramer, 12128 Aboite Rd., Roanoke, Ind. 46783

[21] Appl. No.: 125,465

[22] Filed: Nov. 25, 1987

[51] Int. Cl.$^4$ ............................................. A61F 13/00
[52] U.S. Cl. ..................................... 128/872; 128/876
[58] Field of Search ......................... 128/134, 869–876

[56] References Cited

U.S. PATENT DOCUMENTS

| | | | |
|---|---|---|---|
| 837,373 | 12/1906 | Akers | 128/134 |
| 1,502,276 | 7/1924 | Siebert | 128/134 |
| 2,030,091 | 2/1936 | Behringer | 128/134 |
| 2,333,346 | 11/1943 | Sweetland | 128/134 |
| 2,486,114 | 10/1949 | Cataldo | 128/134 |
| 2,567,082 | 9/1951 | Shuster | 128/134 |
| 2,888,009 | 5/1959 | Taylor | 128/134 |
| 2,940,443 | 6/1960 | Baker | 128/134 |
| 3,136,311 | 6/1964 | Lewis | 128/134 |
| 3,181,530 | 5/1965 | Storey | 128/134 |
| 3,933,154 | 1/1976 | Cabansag | 128/134 |
| 4,050,737 | 9/1977 | Jordan | 297/389 |
| 4,223,670 | 9/1980 | Cramer | 128/134 |

Primary Examiner—Robert A. Hafer
Assistant Examiner—Michael Brown
Attorney, Agent, or Firm—Jeffers, Hoffman & Niewyk

[57] ABSTRACT

A security restraining blanket includes a main flexible flat pad adapted to be secured to a support structure, such as a bed, cart or table, so as to extend across a surface of the structure, and a restraining section adapted to be fastened in a tubular configuration about the torso of a person and attached to the main pad for restraining the person's torso in a desired position on the main pad. Preferably, the restraining section is detachably attached to the main pad by one or more fasteners, such as zippers. Releasable arm restraint straps are provided on the main pad and on the restraining section for securement about the arms of the person to restrain the person's arms in desired positions on the main pad or to the restraining section. The arm straps on the main pad are oriented at about forty-five degrees to the person's torso to restrain the person's arm in a more comfortable position than when the arms are restrained in parallel relation against the sides of the person's torso. Also, releasable fastening straps and segments are provided on the restraining section for securing its opposite ends about the person's torso. Free ends of the straps contain patches of complementary fastening material, such as pile and hook material, for attaching the strap ends together.

14 Claims, 2 Drawing Sheets

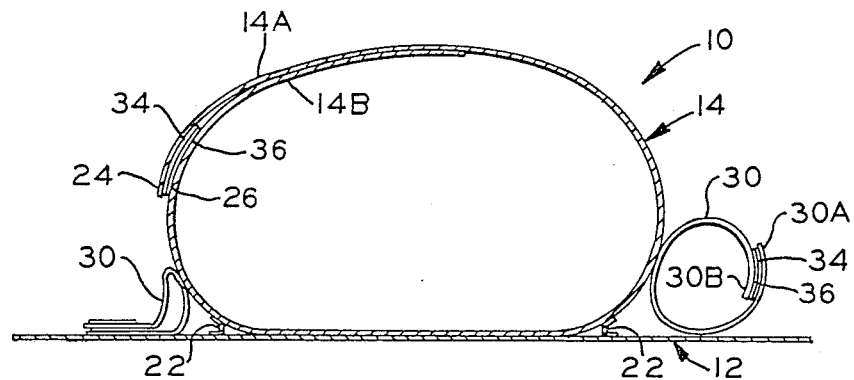
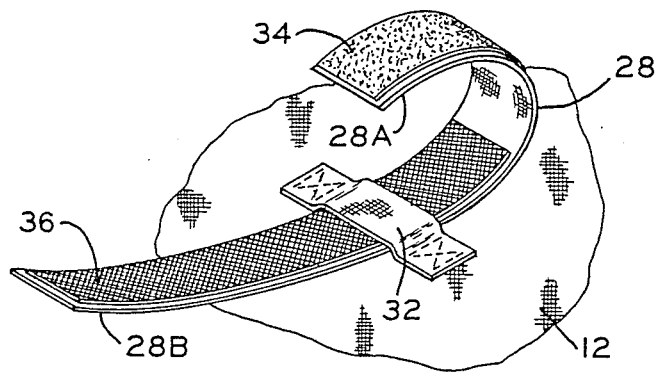
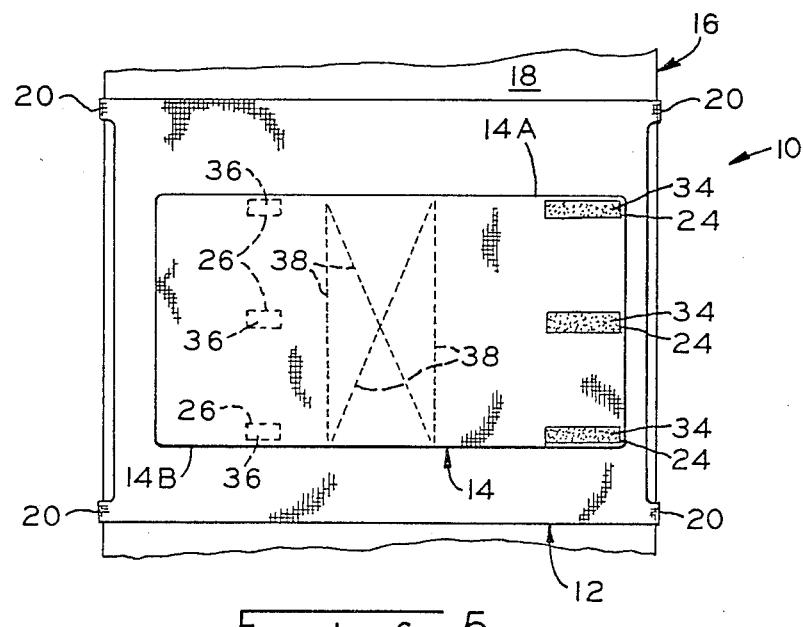

SECURITY RESTRAINING BLANKET

BACKGROUND OF THE INVENTION

1. Field of the Invention

The present invention generally relates to restraining devices used in conjunction with health care procedures and, more particularly, is concerned with a security blanket for restraining a person who has an intravenous tube (IV) or is in traction for a fracture.

2. Description of the Prior Art

Patients, particularly infants and children, typically have to be restrained in some manner to prevent movements which would be detrimental to administering certain types of health care treatments to them. For instance, certain body and arm movements of a patient can interfere with a traction arrangement or can result in removal or infiltration of an IV, causing complications in recovery. Another application for a restraining device would be for children with burns and skin graphs, where restraints are essential to help eliminate wound infections and to keep graphs in place for optimal healing.

However, for a restraining device to be effective, it should not over-restrain the patient, that is, restrain those movements by the patient which would not detrimentally affect the health care treatment. Over-restraint can make the patient more uncomfortable than is necessary and thus reduce his or her ability to tolerate the device for an extended period of time. Over-restraint can also create fear and anxiety, particularly in the case of young patients. Finally, devices which over-restrain a patient typically lack versatility, making them incompatible with the performance of many types of medical procedures.

Absent from the prior art is a restraining device which is comfortable for the patient while, at the same time, effective in restraining only those movements of the patient's torso and arms which would interfere with health care treatments, such as IV therapy or application of traction to a fracture. In fact, no prior art restraints are presently available for children with orthopedic conditions requiring traction for extremities. Restraints are imperative for these children to prevent them from pulling out of alignment with their traction. Also, the child's movements should be carefully controlled during the healing process so that the fractures are held in the correct position for the best possible healing.

Representative of various restraint devices in the prior patent art are the ones disclosed in U.S. Pat. Nos. to Cataldo (2,486,114), Taylor (2,888,009), Storey (3,181,530), Cabansag (3,933,154) and Jordan (4,050,737). These devices are designed to serve different purposes, such as protecting an infant during sleep, immobilizing a child for x-ray and surgical procedures, and restraining a person to a sitting position in a chair. While many of these prior patent art devices generally serve the limited purposes for which they are designed, they do not appear to be suitable for use in conjunction with the types of health care treatments mentioned above.

Consequently, a need exists for a device particularly adapted for minimally restraining the torso and arms of a patient, such as a child, undergoing health care treatments, such as IV therapy or traction.

SUMMARY OF THE INVENTION

The present invention provides a security restraining blanket designed to satisfy the aforementioned needs. The restraining blanket of the present invention is a versatile restraint capable of multiple uses. It is adapted to make health care procedures faster, easier and more comfortable for young patients, although it can also be used by older patients.

The blanket is composed of a main pad and a middle restraining section. The main pad is capable of lying flat against any surface and can be easily applied to any bed, cart or table. The middle restraining section is completely removable from the main pad, or alternatively can be permanently attached thereto. The restraining section in its removable form can be used on the main pad or removed for any required health care treatments or procedures. Both the main pad and restraining section have means for attaching the arms of the patient to them. The patient can be turned from side to side or onto his or her abdomen, without taking off the restraining section. Although not so limited in its applications, the blanket is particularly useful for children receiving IV therapy or those in traction.

Accordingly, the present invention, in one form thereof, is directed to a security restraining blanket, comprising: (a) a main pad adapted to be applied to a support structure so as to extend across a surface of the structure; (b) a restraining section adapted to be applied about the torso of a person and attached to the main pad for restraining the person's torso in a desired position on the main pad; and (c) means on at least one of the main pad and the restraining section and adapted to be applied about at least one of the arms of the person for restraining the person's arm in a desired position on the one of the main pad and the restraining section.

More particularly, the main pad is sheet-like in form and composed of flexible material. Further, the main pad has a plurality of fastening straps for attaching the pad to the support structure. Also, the restraining section is sheet-like in form and composed of a flexible material. The restraining section is detachably attached in an overlying relation to the main pad by releasable fastening means, such as one or more zippers. Alternatively, the restraining section can be permanently attached to the main pad, such as by stitching. Additionally, releasable fastening straps and segments are provided on the restraining section for securement of its opposite ends to apply the restraining section completely about the person's torso.

Further, the restraining means of the blanket is in the form of releasable restraint straps provided on the main pad and on the restraining section for securement about the arms of the person to restrain the person's arms in any of several desired positions on the main pad or on the restraining section. The restraint straps on the restraining section are used to position and restrain the person's arms along one or both sides of the person's torso and of the restraining section encompassing the torso. The restraint straps on the main pad are oriented preferably at about forty-five degrees to the person's torso to restrain the person's arms in a more comfortable angular position than when the arms are restrained generally parallel against the sides of the person's torso.

The free ends of the restraint straps preferably contain patches of complementary fastening material, such as pile and hook material usually referred to as "velcro" material, for attaching the strap ends together. Likewise, the restraining section straps on one end thereof and segments on the other end thereof can contain such patches of fastening material.

In summary then the important benefits derived from the present invention, particularly for a child, are:
(1) the restraint is comfortable and medical procedures can be accomplished faster and more easily;
(2) the child is not overly restrained, which allows for more normal activities and is particularly important when a child must have IV therapy, burn care (such as skin graphs) or traction for an extended length of time;
(3) the child experiences less trauma, with fewer repeated procedures such as:
  (a) surgical intervention to improve alignment of fractures or rebreaking of a fracture which is not healing in proper alignment;
  (b) surgical procedures to reapply skin graphs;
  (c) repositioning of traction;
  (d) restarting IV's and other painful procedures; and
(4) the restraint provides a feeling of security for the child as the security blanket surrounds the child causing the child to become more relaxed, calm, and generally less needful of medication for pain and muscle spasms.

These and other advantages and attainments of the present invention will become apparent to those skilled in the art upon a reading of the following detailed description when taken in conjunction with the drawings wherein there is shown and described an illustrative embodiment of the invention.

BRIEF DESCRIPTION OF THE DRAWINGS

In the course of the following detailed description, reference will be made to the attached drawings in which:

FIG. 3 is a sectional view taken along line 3—3 of FIG. 2. FIG. 4 is an enlarged perspective view of one of the arm restraint straps of the blanket and the loop connecting the strap to the main pad of the blanket.

FIG. 5 is a top plan view of the restraining blanket similar to that of FIG. 2, but with the restraining section of the blanket being in an unfastened open condition and stitched permanently to the main pad.

DETAILED DESCRIPTION OF THE INVENTION

Figure 1:
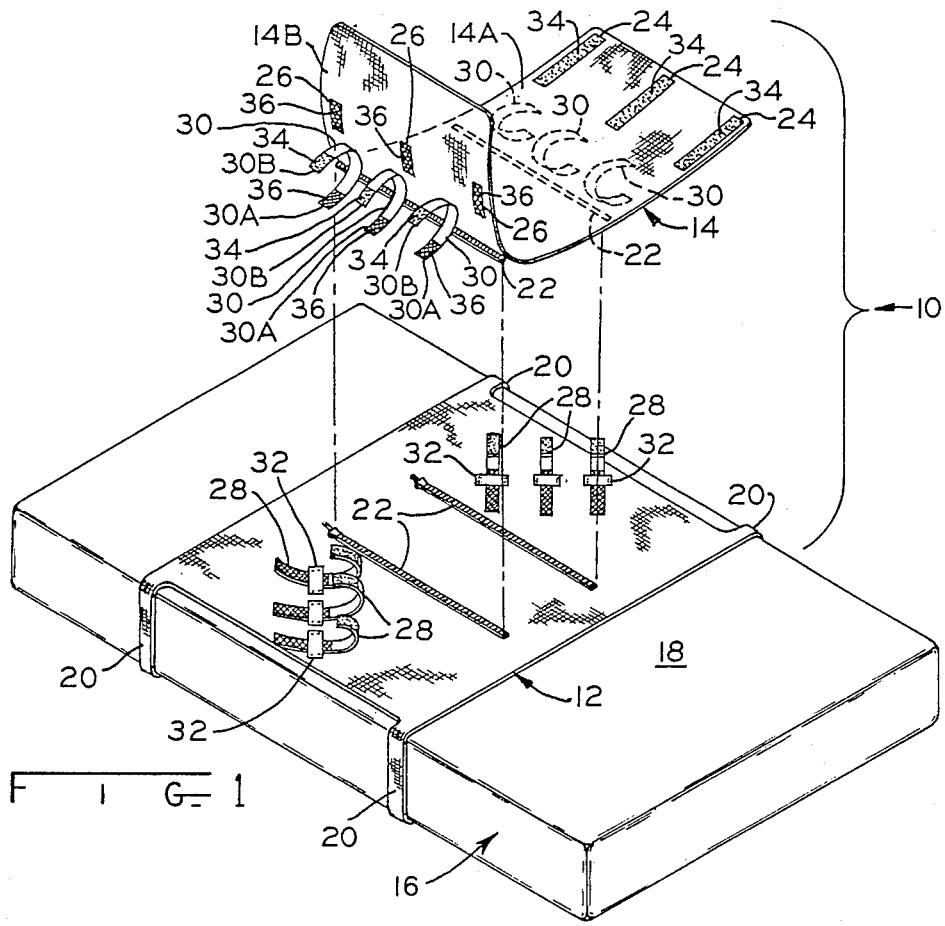
FIG. 1 is a perspective view, with some parts in exploded form, of a security restraining blanket constructed in accordance with the present invention.
Figure 2:
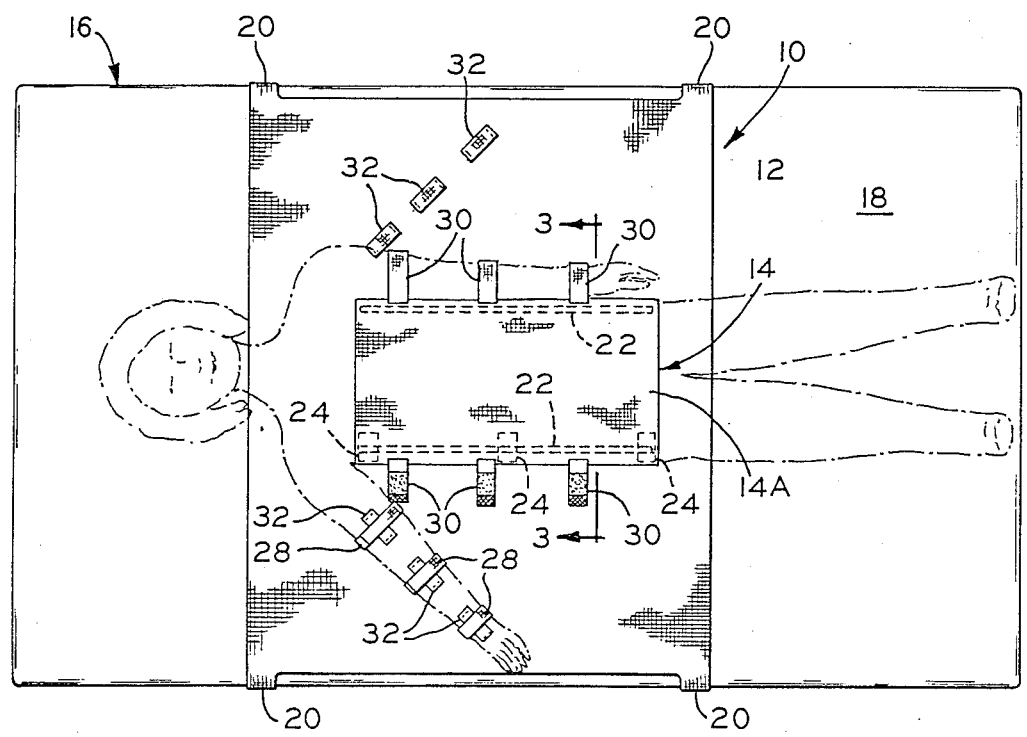
FIG. 2 is a top plan view of the restraining blanket of FIG. 1, illustrating the restraining section of the blanket applied in a fastened condition about the torso of a child being shown in phantom line form and illustrating respective arm restraint straps on the main pad and on the restraining section of the blanket being fastening about the arms of the child.

Referring now to the drawings, and particularly to FIGS. 1, 2 and 5, there is shown a security restraining blanket, generally designated by the numeral 10, providing the preferred embodiment of the present invention. The restraining blanket 10 basically includes a main flat pad 12 and a vest-like restraining section 14. The main pad 12 is adapted to be applied to a support structure 16, such as a bed mattress, cart or table, so as to extend across a surface 18 of the structure 16. The restraining section 14 is adapted to be applied in a tubular configuration (see FIG. 4) about the torso of a person, as seen in FIG. 2, and attached to the main pad 12 for restraining the person's torso in a desired position on the main pad 12.

More particularly, the main pad 12 is sheet-like in form and composed of flexible material. Further, the main pad 12 has a plurality of elongated fastening straps 20 for attaching the pad 12 to the support structure 16 in any suitable manner. For example, the straps 20 are placed around the lower side of the support structure 16, or mattress as seen in FIG. 1, and then pulled taut and secured together by a snap clip (not shown).

The restraining section 14 is sheet-like in form and composed of a flexible material. The restraining section 14 is detachably attached in an overlying relation to the main pad 12 by releasable fastening means 22, such as one or more zippers. Alternatively, the restraining section 14 can be permanently attached to the main pad 12, such as by stitching 38 as shown in FIG. 5. Additionally, as also shown in FIG. 3, releasable fastening straps 24 and segments 26 are provided on the restraining section 14 for securement of its opposite ends 14A, 14B to apply the restraining section 14 in a vest-like fashion completely about the patient's torso, from approximately the upper buttock region up to the patient's axilla region. Preferably, the flexible material composing the main pad 12 and the restraining section 14 of the blanket 10 is a Kodel (trademark) polyester and cotton blend which is machine washable.

The blanket 10 also includes restraining means on the main pad 12 and on restraining section 14 adapted to be applied about the arms of the patient for restraining the patient's arms in desired positions either on the main pad 12 or to the restraining section 14. The restraining means take the form of releasable restraint straps 28, 30 provided respectively on the main pad 12 and on the restraining section 14 for securement about the arms of the patient in order to restrain the patient's arms in any of several desired positions on the main pad 12 or on the restraining section 14. The restraint straps 30 on the restraining section 14 are used to position and restrain the patient's arms along the sides of the patient's torso and of the restraining section 14 encompassing the torso. The restraint straps 28 on the main pad 12 are oriented preferably at about forty-five degrees to the patient's torso to restrain the patient's arms in a more comfortable angular position than when the arms are restrained generally parallel against the sides of the patient's torso. FIG. 4 depicts how one of the arm restraint straps 28 on the main pad 12 of the blanket 10 is held to the main pad by a loop 32 connected to the main pad. The Velcro strap 28 extends through the loop 32.

The free ends 28A, 28B and 30A, 30B of the restraint straps 28 and 30 have suitable fastening elements affixed thereon. In the one illustrated embodiment, the fastening elements for attaching the strap ends together are patches 34, 36 of complementary fastening material, such as pile and hook material commercially available under the trademark, Velcro. Likewise, the restraining section straps 24 on one end 14A thereof and the segments 26 on the other end 14B thereof have such patches 34, 36 of complementary fastening material affixed thereon.

In FIG. 2, the restraining section 14 of the blanket 10 is illustrated applied in a fastened condition about the torso of a patient. One set of arm restraint straps 28 on one side of the main pad 12 and one set of arm restrain straps 30 on an opposite side of the restraining section 14 are fastened about the patient's arms to restrain the arms in the illustrated positions. FIG. 5 shows the restraining section 14 of the blanket 10 in an unfastened open condition prior to placing the patient thereon.

Typically, one or both arms of a patient with an IV would be restrained against the main pad 12 by the restraint straps 28 thereof and at the forty-five degree angle to the patient's torso for maximum comfort when the patient is resting in a bed and when the restraining section 14 is attached to the main pad 12. On the other hand, if the patient is to be moved for performance of some other medical procedure such as an X-ray or to be placed in a chair, restraint of the patient's arm is changed to the straps 30 to restrain the arm against the patient's torso. The restraining section 14 can then by detached by unzipping it from the main pad 12. The patient's arm with the IV will still be adequately restrained even though the patient has now become mobilized for undertaking other medical procedures or activities.

FIG. 5 illustrates the restraining blanket wherein the restraining section 14 is permanently secured to the main pad 12 by means of stitching 38 thus restraining section 14 may not be detached from the main pad 12.

An advantage in the use of a pair of zippers 22 to attach the restraining section 14 to the main pad 12 is that the patient can be shifted to lay on his or her side by unfastening the appropriate one of the zippers and placing a pillow under the released side of the patient. The main advantage of the blanket 10 as compared to prior art devices is the comfort it achieves by not over-restraining the patient. It permits considerable degrees of freedom of movement of the patient even while the patient is restrained sufficiently to guard against disruption of the particular health care treatment. What contributes to the patient's comfort is that only the patient's torso is held by the restraining section 14 to the main pad 12.

It is thought that the present invention and many of its attendant advantages will be understood from the foregoing description and it will be apparent that various changes may be made in the form, construction and arrangement of the parts thereof without departing from the spirit and the scope of the invention or sacrificing all of its material advantages, the form hereinbefore described being merely preferred or exemplary embodiments thereof.

What is claimed is:

1. A security restraining blanket, comprising:
   (a) a sheet-like main pad composed of flexible material and adapted to be applied to a support structure so as to extend across a surface of said structure, said main pad including a plurality of straps for attaching said pad to said support structure;
   (b) a sheet-like restraining section composed of flexible material and adapted to encircle only the torso of a person for restraining the person's torso in a desired position on said main pad, said restraining section adapted not to encircle the person's neck and arms, said restraining section releasably secured to said main pad by releasable fastening means whereby a person may be moved from said main pad without removing said person from said restraining section;
   (c) arm restraining means on said main pad and adapted to be applied about at least one of the arms of the person for restraining the person's arms in a desired position on said main pad; and
   (d) releasable fastening straps and segments attached on opposite end portions of said restraining section for securement of the opposite end portions of said restraining section together after said section is applied about the person's torso.

2. The blanket as recited in claim 1, further comprising:
   (d) releasable fastening means detachably attaching said restraining section in an overlying relation to said main pad.

3. The blanket as recited in claim 2, wherein said fastening means is a zipper.

4. The blanket as recited in claim 2, wherein said fastening means is a pair of spaced zippers.

5. The blanket as recited in claim 1, wherein said straps and segments contain patches of complementary pile and hook fastening material for attaching ends of said strap and said segments together.

6. The blanket as recited in claim 1, wherein said arm restraining means is in the form of releasable restraint straps provided on both said main pad and on said restraining section for securement about the arms of the person to restrain the person's arms in any of several desired positions on said main pad or to said restraining section.

7. The blanket as recited in claim 12, wherein said restraint straps on their free ends contain patches of complementary pile and hook fastening material for attaching said strap ends together and wherein said restraint straps provided on said main pad are connected thereon by loops of material attached to said main pad and through which extend said restraint straps.

8. A security restraining blanket, comprising:
   (a) a sheet-like main pad composed of flexible cloth material and adapted to be secured to a support structure so as to extend across a surface of said structure, said main pad including a plurality of straps for attaching said pad to said support structure;
   (b) a sheet-like restraining section composed of flexible cloth material and adapted to be fastened about only the torso of a person and detachably secured to said main pad for restraining a person's torso in a desired position on said main pad, said restraining section adapted not to encircle the person's neck and arms;
   (c) releasable fastening means on said main pad and said restraining section for detachably securing said restraining section in an overlying relation to said main pad; and
   (d) arm restraining means on both said main pad and said restraining section and adapted to be fastened about at least one of the arms of a person for restraining the person's arms in a desired position on either said main pad or said restraining section.

9. The blanket as recited in claim 8, wherein said main pad has a plurality of straps for attaching said pad to said support structure.

10. The blanket as recited in claim 8, wherein said restraining section has releasable fastening straps and segments attached on opposite end portions thereof for securement of its opposite end portions together after said section is applied about the person's torso.

11. The blanket as recited in claim 10, wherein said straps and segments contain patches of complementary pile and hook fastening material for attaching ends of said strap and said segments together.

12. The blanket as recited in claim 8, wherein said fastening means is a pair of spaced zippers.

13. The blanket as recited in claim 8, wherein said restraining means is in the form of flexible releasable restraint straps provided on both said main pad and on said restraining section for securement about the arms of a person to restrain the person's arms in any of several desired positions on said main pad or to said restraining section.

14. The blanket as recited in claim 13, wherein said restraint straps on their free ends contain patches of complementary pile and hook fastening material for attaching said strap ends together and wherein said restraint straps provided on said main pad are connected thereon by loops of material attached to said main pad and through which extend said restraint straps.

* * * * *